United States Patent
Kiliaan et al.

(10) Patent No.: US 6,730,661 B1
(45) Date of Patent: May 4, 2004

(54) NUTRITIONAL COMPOSITION WHICH CONTAIN NON-DIGESTIBLE POLYSACCHARIDES AND USE THEREOF TO REDUCE TRANSPORT THROUGH TIGHT JUNCTIONS

(75) Inventors: Amanda Johanne Kiliaan, Wageningen (NL); Jacques Alphons Groot, Heiloo (NL); Johannes Wilhelmus Timmermans, Ede (NL); Jan Van Der Meulen, Dronten (NL); Katrien Maria Jozefa Van Laere, Heteren (NL); Pieter Brandt Bijlsma, Amsterdam (NL)

(73) Assignee: N. V. Nutricia, Zoetermeer (NL)

( * ) Notice: Subject to any disclaimer, the term of this patent is extended or adjusted under 35 U.S.C. 154(b) by 0 days.

(21) Appl. No.: 10/089,371

(22) PCT Filed: Sep. 29, 2000

(86) PCT No.: PCT/NL00/00697

§ 371 (c)(1),
(2), (4) Date: Jul. 16, 2002

(87) PCT Pub. No.: WO01/33975

PCT Pub. Date: May 17, 2001

(30) Foreign Application Priority Data

Sep. 29, 1999 (NL) .............................. 1013175

(51) Int. Cl.⁷ ..................... A61K 31/715; A61K 31/721
(52) U.S. Cl. ........................... 514/23; 536/4.4; 536/51; 536/123.1
(58) Field of Search ............................ 514/23, 21, 782, 514/783, 59; 536/4.4, 51, 112, 123.1

(56) References Cited

U.S. PATENT DOCUMENTS 5,260,279 A  * 11/1993  Greenberg ................... 514/21

FOREIGN PATENT DOCUMENTS

| EP | 0 153 013 | | 8/1985 | |
| EP | 0 385 598 | | 9/1990 | |
| GB | 0153013 A2 | * | 8/1985 | .......... A61K/47/00 |
| WO | WO 00/57717 | | 10/2000 | |

* cited by examiner

Primary Examiner—James O. Wilson
Assistant Examiner—Ganapathy Krishnan
(74) Attorney, Agent, or Firm—Young & Thompson

(57) ABSTRACT

The present invention relates to the use of one or more non-digestible polysaccharides selected from the group consisting of dextrans having a molecular weight of 8 kD to 40,000 kD, hydrolysed (gluco)mannans having a molecular weight of 0.5 kD to 1,000 kD and hydrolysed (galacto) mannans having a molecular weigth of 0.5 kD to 1,000 kD for the preparation of a nutritional composition to reduce the uptake of high molecular weight substances, allergens and microorganisms through the intestinal wall, more particularly to reduce transport of high molecular weight substances, allergens and microorganisms through the tight junctions in the intestines, the rise in the viscosity of the nutritional composition caused by the polysaccharides being less than 20 mPa.s. The nutritional compositions can be used to prevent or to treat allergy, allergic reactions, sepsis and inflammatory processes, such as can arise under emotional and physical stress, ischaemia, reperfusion damage during and after operations, after radiation treatment and/or chemotherapy of cancer patients and in the case of inflammatory diseases of the intestine, diarrhoea and allergies.

7 Claims, 3 Drawing Sheets

Figure 1:
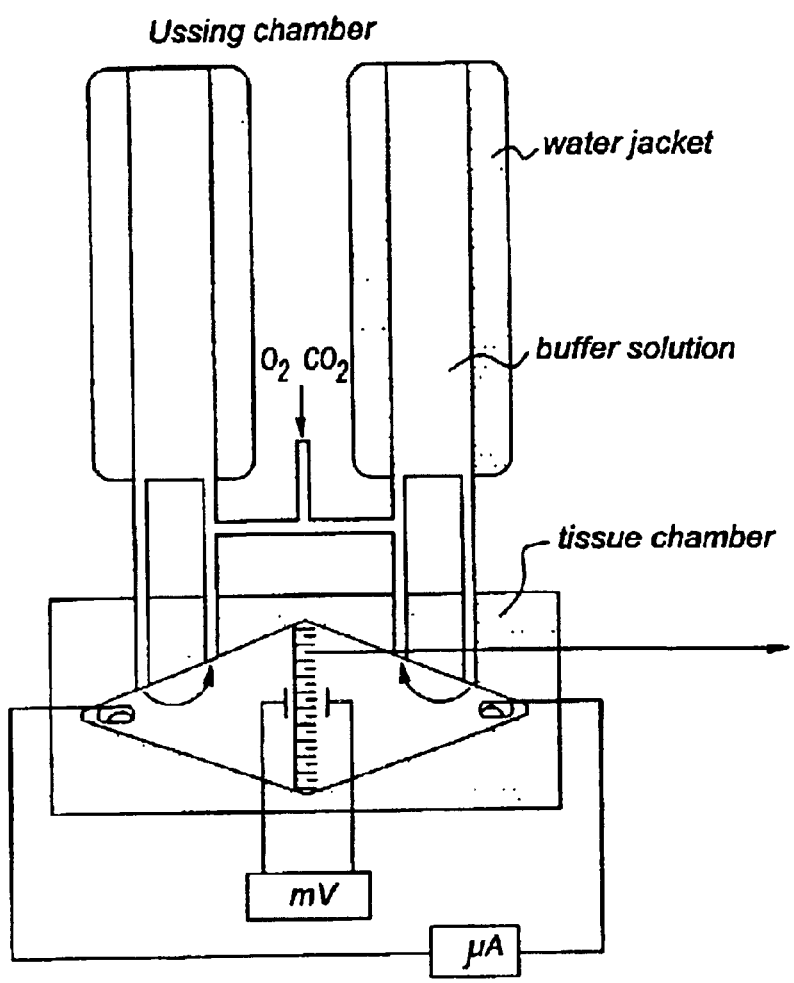

NUTRITIONAL COMPOSITION WHICH CONTAIN NON-DIGESTIBLE POLYSACCHARIDES AND USE THEREOF TO REDUCE TRANSPORT THROUGH TIGHT JUNCTIONS

The present invention relates to nutritional compositions which contain a specific class of non-digestible dextrans, hydrolysed (galacto)mannans and/or hydrolysed (gluco) mannans. These compositions reduce the uptake of high molecular weight substances, allergens and microorganisms through the intestinal wall. In particular, the present invention relates to reduction of the free transport of such substances through the tight junctions (TJ) of the intestines, without the transport of low molecular weight substances, such as nutrients, via the intestinal epithelium being impeded. The compositions can be used to prevent the increased permeability of the intestinal wall, resulting from various causes, and the penetration of toxins, antigens and pathogenic microorganisms present in the lumen which is caused as a result.

The structure and function of tight junctions is described, inter alia, in Ann. Rev. Physiol. 60, 121–160 (1998) and in Ballard T. S. et al., Annu.Rev.Nutr., 1995, 15:35–55. Tight junctions do not form a rigid barrier but play an important role in the diffusion through the intestinal epithelium from lumen to bloodstream and vice versa.

The permeability of the tight junctions is highly regulated and can be disturbed by illness and certain toxins in the lumen. Regulation takes place from the nervous system, the hormonal system and the immune system. When the tight junctions open, substances which have a high molecular weight, allergens and even microorganisms will pass through the tight junctions. The translocation of substances having a high molecular weight can under certain circumstances give rise to sensitisation of the immune system and result in allergic reactions on subsequent exposure. Translocation of pathogenic microorganisms imposes greater strain on the immune system and can make persons and animals ill, inter alia in periods of lowered resistance. The same applies, for example, in the case of bacterial toxins which have been able to pass through the epithelial layer and have been able to reach the bloodstream.

The invention now relates to the use of one or more non-digestible polysaccharides selected from the group consisting of dextrans having a molecular weight of 8 kD to 40,000 kD, hydrolysed (gluco)mannans having a molecular weight of 0.5 kD to 1,000 kD and hydrolysed (galacto) mannans having a molecular weight of 0.5 kD to 1,000 kD to reduce the uptake of high molecular weight substances, allergens and microorganisms through the intestinal wall, with the proviso that the rise in the viscosity of the nutritional composition caused by the polysaccharides is less than 20 mPa.s.

More particularly, the invention relates to the use of the abovementioned compositions to reduce transport of high molecular weight substances, allergens and microorganisms through the tight junctions in the intestines.

In addition to reducing the transport of harmful substances and microorganisms to a significant extent, a significant advantage of the present invention is that the normal transport of useful substances (nutrients) such as glucose, amino acids, dipeptides or trace elements is virtually maintained.

According to the invention non-digestible polysaccharides are understood to be polysaccharides which are not, or are barely, digested or converted by the human digestive enzymes under the conditions prevailing in the body. It should be pointed out that some of the non-digestible polysaccharides can be fermented by the microorganisms present in the intestines (colon, caecum and part of the ileum). Without wishing to be tied to any theory, it is, however, expected that the effect of the polysaccharides on the paracellular transport does not take place via the fermentation products.

The degree to which the polysaccharides are digested can be established using the method as described in Minekus, M., Ph.D. Thesis, University of Utrecht, 1998, Development and validation of a dynamic model of the gastrointestinal tract, Section 2. The polysaccharides according to the invention are less than 50% digestible and preferably less than 30% digestible.

Dextrans according to the invention are understood to be dextrans obtained via a (bio)synthetic route or naturally occurring dextrans. The molecular weight of such dextrans can be regulated by partial acid or enzymatic hydrolysis of the molecule followed by repeated fractionation and precipitation with alcohol or ultrafiltration. These methods, which are known per se to those skilled in the art, must be carried out in such a way that the molecular weight of the dextrans falls within the cited range of 8 kD to 40,000 kD.

Dextrans having a molecular weight of 20 kD to 2,000 kD are preferably used.

The term (gluco)mannans is used to refer both to the mannans and the glucomannans. The same applies in the case of the (galacto)mannans. Examples of galactomannans are guar gum, locust bean gum and tara gum. These (galacto) mannans and (gluco)mannans are used in the hydrolysed form. The molecular weights are between 0.5 kD and 1,000 kD.

Mixtures of dextrans, (galacto)mannans and (gluco) mannans can also be used.

The hydrolysed (galacto)mannans or (gluco)mannans according to the invention can be obtained by partial, but extensive, hydrolysis, for example with the aid of enzymes suitable for this purpose, by means of which substantial quantities of oligosaccharides having a chain length of 3 to 5,600, preferably of 4 to 1,000, are produced.

The polysaccharides are preferably present in the preparation in an amount such that the concentration of these polysaccharides in the intestines is 0.1 to 20 g/l, preferably 0.5 to 10 g/l and preferentially 1 to 6 g/l. The minimum quantity of the active ingredient is determined in that a significant decrease in the transport through the tight junctions is detected.

It is not necessary for the polysaccharides to be administered at that location where the paracellular transport is disturbed. The presence of the active component at a location somewhere in the intestines between the stomach and the affected location is sufficient.

Some of the polysaccharides used according to the invention have a viscosity-increasing action which could prevent the absorption of nutritional components. The preparation must have a composition such that the normal transcellular transport is not impeded.

More particularly, the nutritional composition according to the invention has a viscosity of less than 100 mPa.s, preferably less than 40, but even more preferentially less than 30 mPa.s. For the present invention it is important in particular that the polysaccharides, independently of the other constituents of the composition, have only a low viscosity-increasing effect. The viscosity-increasing effect of the active polysaccharides in the composition must be less than 20 and preferably less than 10 mPa.s and can be, for example, 3 mPa.s. Thus, the major proportion of the viscosity of the product is caused by components other than the polysaccharides in the product.

The viscosity is determined by means of a Carri-med at a shear rate of 100 per second and at 20° C.

In the case of dry products the viscosity limits described above apply after reconstitution of the product.

In general, therefore, the type of polysaccharide (molecular weight) and the concentration thereof will be so chosen that an optimum combination of effectiveness and viscosity is obtained. Not only molecule size, but also degree of branching and degree of loading determine action, viscosity and/or fermentation behaviour.

The polysaccharides according to the invention prevent the free transport of high molecular weight substances, allergens and microorganisms through the tight junctions of the intestinal wall. In this context high molecular weight substances are understood to be the substances which under normal conditions are not able to pass through the tight junctions, or are able to do so only in minor amounts, and which can be assumed to have a toxic or allergenic action. These substances will in general have a molecular size of above 4,000 Dalton. Antigens, substances which activate the immune system, are in general peptides, which may or may not have been glycosided, frequently with a molecular weight of more than 10,000 Dalton. Allergens are antigens which produce an allergic reaction which usually is mediated via immunoglobulin E.

In this context microorganisms are understood to be in particular microorganisms which occur in the intestinal lumen. Thus, for example, under certain conditions overgrowth of microorganisms can take place in the small intestine, as a result of which tight junctions are to an increased extent exposed to these microorganisms.

According to another aspect of the invention foods or preparations are proposed which contain these non-digestible polysaccharides. These foods can be:

complete foods;
food supplements;
health-promoting preparations; and
tube feeds.

The compositions according to the invention can be used to prevent or to treat specific types of allergy, allergic reactions, sepsis and inflammatory processes, such as can arise under emotional and physical stress, ischaemia, reperfusion damage during and after operations, after radiation treatment and/or chemotherapy of cancer patients and in the case of inflammatory diseases of the intestine, diarrhoea and allergies.

The complete foods and food supplements described above can in particular be used in the treatment of, or to prevent, inflammatory diseases of the intestines, such as colitis ulcerosa, inflammatory bowel disease and Crohn's disease. Specific other constituents which can be incorporated in such foods and supplements are growth hormones, glutamine, n–3 LCPUFAs and the requisite contents of macro-and microingredients.

Furthermore, the foods according to the invention can be used before and after operations. Specifically, ischaemia and reperfusion damage to the intestine often occur during operations, as a result of which the tight junctions open. Introducing the polysaccharides according to the invention into the intestines before and after the operation could prevent the uncontrolled paracellular transport. The administration of these polysaccharides can also be beneficial after chemotherapy.

In the case of diarrhoea a number of pathomorphological changes can also arise which are associated with an increased permeability of the tight junctions. These changes can arise with specific types of diarrhoea. The complete foods and food supplements according to the invention can be used to counteract the adverse consequences of this increased permeability.

The tight junctions can also open during stress, both of a physical nature (for example endurance sports) and of an emotional nature, as a result of which bacterial translocation takes place. Examples of emotional stress under which this takes place is the stress which arises during the transport of pigs to the slaughter house. Contamination of the meat can occur as a result. Another example is the stress that occurs when weaning piglets. The polysaccharides can be administered before the stress takes place, during stress or after the stress has taken place.

With the aid of the polysaccharides according to the invention it is also possible to prepare preparations which are suitable for patients who have a food allergy, such as an allergy to cow's milk or to gluten. The increase in the permeability as a result of exposure to the allergen can be prevented. These preparations are of such composition that they do not contain the said allergens.

Figure 2:
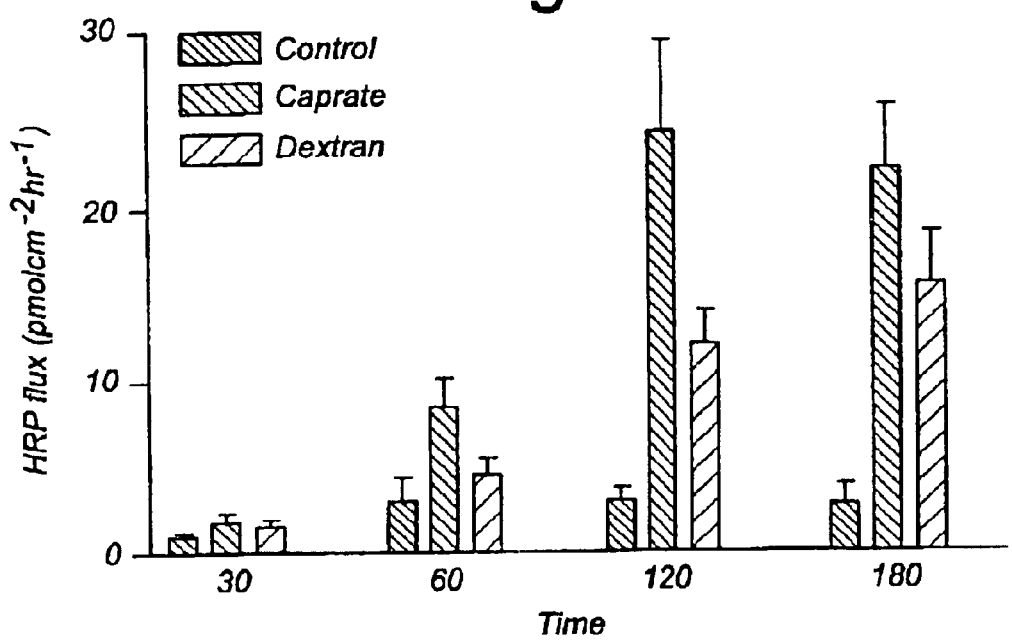
Figure 3:
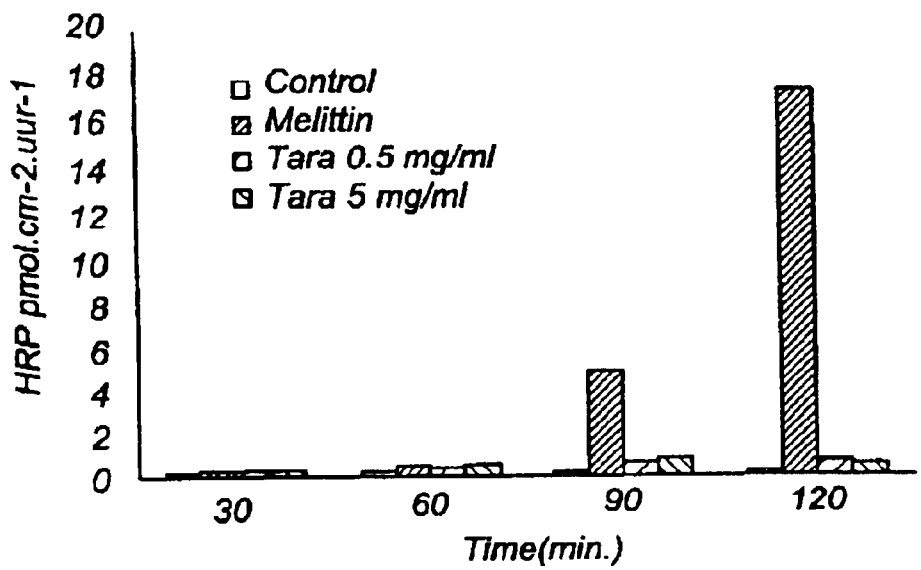
Figure 4:
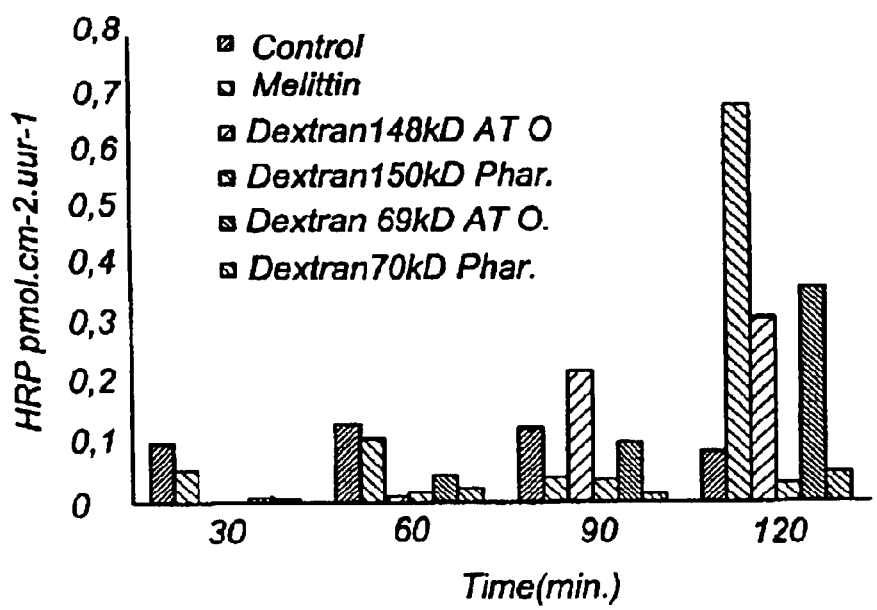
Figure 5:
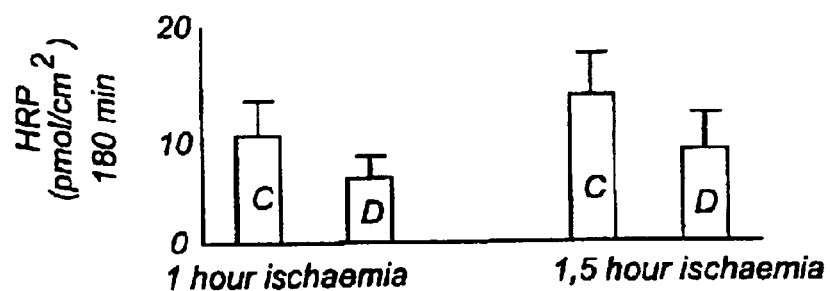
Figure 6:
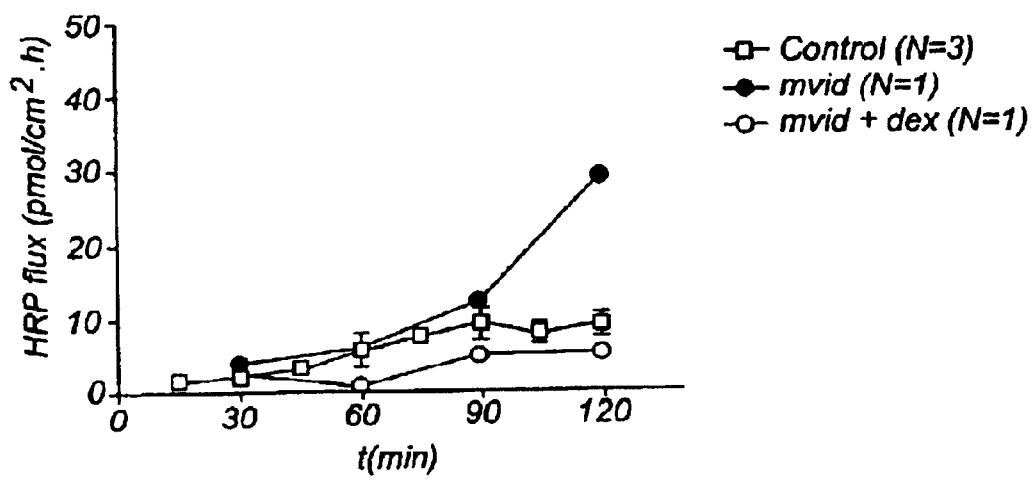

The invention is explained on the basis of the following examples and with reference to the appended figures, in which FIG. 1 shows the Ussing chamber used in the examples;
FIG. 2 shows the inhibition of the effects of caprate by dextran;
FIG. 3 shows the inhibition by hydrolysed tara gum of the increased paracellular permeability caused by melitin;
FIG. 4 shows the effect of dextrans on the HRP flow;
FIG. 5 shows the effect of dextrans on the HRP flow in a pig under anaesthesia;
FIG. 6 shows the effect of dextran on the increased permeability of the intestine of a microvillus inclusion patient.

EXAMPLES

I Examples of Products

Examples of compositions of various types of products in which the active component is dextran are given below.

The various types of product can be complete enteral foods, for use by the patient him or herself or for use as a tube feed. The product can be either in liquid form or in powder form, which is ready for use after dissolving. The active components can also be used as an ingredient in another food (for example bread) or in food supplements, such as a bar, a dairy product such as yoghurt, or a powder in the form of a sachet.

Example 1

Ready-to-feed, liquid, complete food for use before or after operations.

The composition is as follows per 100 ml of the product:

| | |
|---|---|
| Protein: | 7.0 g |
| Fat: | 4.0 g |
| Carbohydrate: | 21 g |
| Dextran: | 0.2 g |

Minerals in a quantity of ¹⁄₁₅th of the recommended daily allowance (=RDA) can be added per 100 ml of the product. Trace elements and vitamins are added in somewhat larger amounts, i.e. ²⁄₁₅ RDA. The product is of a composition such that 1,500 ml has to be consume by the patient.

Example 2

Complete tube feed for persons suffering from inflammatory bowel disease. Per 100 ml the product contains:

Protein based on casein 7.0 g

Fat based on vegetable oils and 10% fish oil and 20% MCT; the linoleic acid content is 20% and the alpha-linolenic acid content 4.5%

Premixes containing the conventional forms of trace elements, vitamins and minerals Na, K, Ca, Mg, P, Zn, Fe, Mn, Cu, vit. B1, B2, niacin, A, D, K, B6, B12, pantothenic acid, folic acid.

Dextran: 0.6 g

Example 3

Food supplement for patients suffering from food intolerance or allergy.

Yoghurt based on soya milk. Per 100 ml the yoghurt contains:

Protein 4.0 g, fat 3.9 g, carbohydrates 12.3 g and 0.1 RDA of vitamins and trace elements.

Na=80; K=135; Cl=125; Ca=50; P=50; Mg=20 mg

Hydrolysed galactomannans 0.5 g

Example 4

Energy drink for athletes.
Per 100 ml the liquid contains

| | |
|---|---|
| Carbohydrate: | 7.0 g |
| Glucose: | 0.2 g |
| Fructose: | 1.8 g |
| Lactose: | 0.4 g |
| Sucrose: | 1.7 g |
| Polysaccharides: | 2.5 g |
| Organic acids: | 0.4 g |
| Minerals: | |
| Na: | 37 mg |
| K: | 17 mg |
| Cl: | 58 mg |
| Ca: | 8 mg |
| Mg: | 1 mg |
| Vitamin C: | 15 mg |
| Dextran | 0.1 g |

Example 5

Premix for use in pig or piglet feed.

A/Premix consisting of 90% cornflour and 10% 150 kD dextran

B/Premix consisting of a suitable premix of vitamins, trace elements and minerals and 10% dextran.
Premix A or B, or mixtures thereof, can be used in the production of pig feeds. These can be special feeds for use when pigs are transported, have to be rehoused in the sty or if they have a period of lowered resistance.

The premixes can also be used in a piglet feed for use after weaning, as an additive or instead of the premixes which are already known for use in piglet feed.

II Effect on Transport via the Tight Junctions of the Intestine

Use was made of a model set-up for determination of the effect of the polysaccharides used.

A test animal, such as a rat or guinea pig, was brought under narcosis. The stomach wall was then opened and a piece of the ileum tied off. The intestinal tissue was removed and stripped of layers of muscle. The preparation thus obtained was then stretched between two compartments through which oxygenated solutions flowed (FIG. 1). The preparation was treated either with buffer (control or blank) or caprate in buffer in order to open the tight junctions (100% permeability) or with the combination of caprate and a certain concentration of polysaccharide in buffer. As a measure of the permeability the transport of HRP (horseradish peroxidase) over the preparation was determined in accordance with known methods.

The results of this type of experiments are shown in FIGS. 2 to 5.

The in vitro effect of dextran (70 kD) on the increased HRP flow caused by caprate in a guinea pig intestinal epithelium is shown in FIG. 2.

The in vitro effect of hydrolysed tara gum (900 D) on the HRP flow of Caco-2 cells under the influence of 2 $\mu$M melitin is shown in FIG. 3. It can be seen that the increased paracellular permeability caused by melitin is inhibited by tara gum.

The effect of various dextrans on the HRP flow of Caco-2 cells under the influence of 2 $\mu$M melitin is shown in FIG. 4. Phar in the figure stands for Pharmacosmos.

FIG. 5 shows the effect of dextran on the increased HRP flow in the pig intestine caused by ischaemia. The figure relates to experiments with a pig under full narcosis, in which segments of the caudal section of the jejunum were taken. The effect of 5.6 g/l dextran (70 kD)(D) in the in situ ischaemia reperfusion model in pigs as a function of the duration of ischaemia was determined in comparison with control (C) where no dextran was introduced into the lumen during ischaemia. A significant fall in the HRP flow under the influence of dextran was found compared with the control value.

Suction biopsies were taken from the duodenum of a child suffering from microvillus inclusion disease (MVID). In the Ussing chamber these preparations displayed a four-fold increase in permeability to HRP compared with the normal value. After adding 70 kD dextrans to the luminal compartment of the Ussing chamber to give a concentration of 4.2 g/l the permeability was reduced to the normal level. No further HRP could be detected in the paracellular spaces or tight junctions by means of electron microscopy. A corresponding result was obtained with dextrans having a molecular weight of 150 kD.

FIG. 6 shows the result of this experiment with dextrans having a molecular weight of 70 kD. After 120 minutes a clear difference is detectable in the permeability with and without the addition of dextrans.

What is claimed is:

1. A method of reducing the uptake of molecular weight substances above 4000 Da, allergens and microorganisms through the intestinal wall, comprising administering to a mammal in need thereof a nutritional composition containing a polysaccharide selected from the group consisting of dextrans having a molecular weight of 8 kD to 40,000 kD, hydrolysed glucomannans having a molecular weight of 0.5 kD to 1,000 kD and hydrolysed galactomannans other than guar gum or hydrolysed guar gum, having a molecular weight of 0.5 kD to 1,000 kD, the polysaccharide being present in the nutritional composition only in an amount to cause an increase in the viscosity of the nutritional composition which is less than 10 m.Pa.s.

2. A method as claimed in claim 1, wherein the polysaccharide is selected from dextrans having a molecular weight of 20 kD to 2,000 kD.

3. A method as claimed in claim 1, wherein the nutritional composition is a complete food.

4. A method as claimed in claim 1, wherein the nutritional composition is a food supplement.

5. A method as claimed in claim 1, wherein the uptake reduction occurs at the tight junctions of the intestinal wall.

6. A method as claimed in claim 1, wherein said mammal suffers from allergies, allergic reactions, and inflammatory processes, which can arise under emotional and physical stress, ischaemia, reperfusion damage during and after operations, and after radiation treatment and/or chemotherapy of cancer patients.

7. A method as claimed in claim 1, wherein the nutritional composition is administered in a quantity such that the concentration of polysaccharide in the intestine is 0.1 to 6 g/l.

* * * * *